(12) United States Patent
Owen

(10) Patent No.: US 10,139,329 B2
(45) Date of Patent: Nov. 27, 2018

(54) PARTICLE SIZE DETERMINATION USING RAMAN SPECTROSCOPY

(71) Applicant: Kaiser Optical Systems Inc., Ann Arbor, MI (US)

(72) Inventor: Harry Owen, Franklin, MI (US)

(73) Assignee: Kaiser Optical Systems Inc., Ann Arbor, MI (US)

( * ) Notice: Subject to any disclaimer, the term of this patent is extended or adjusted under 35 U.S.C. 154(b) by 0 days.

(21) Appl. No.: 15/784,703

(22) Filed: Oct. 16, 2017

(65) Prior Publication Data

US 2018/0106712 A1   Apr. 19, 2018

Related U.S. Application Data

(60) Provisional application No. 62/408,108, filed on Oct. 14, 2016.

(51) Int. Cl.
| | | |
|---|---|---|
| *G01J 3/00* | (2006.01) | |
| *G01N 15/02* | (2006.01) | |
| *G01N 15/14* | (2006.01) | |
| *G01N 21/65* | (2006.01) | |
| *G01N 21/85* | (2006.01) | |

(52) U.S. Cl.
CPC ..... *G01N 15/0211* (2013.01); *G01N 15/1434* (2013.01); *G01N 21/65* (2013.01); *G01N 21/8507* (2013.01); *G01N 2015/1486* (2013.01)

(58) Field of Classification Search
CPC ........ G01J 3/28; G01J 3/44; G01J 3/02; G01J 3/00; G01J 3/18; G02B 27/42; G02B 23/26; G02B 23/24; G02B 5/18; G01B 9/02; G01N 15/0211; G01N 15/1434
See application file for complete search history.

(56) References Cited

U.S. PATENT DOCUMENTS

| | | | |
|---|---|---|---|
| 2004/0004714 A1 | 1/2004 | Owen et al. | |
| 2004/0233425 A1* | 11/2004 | Long ............ | B01J 8/1809 356/301 |
| 2012/0041689 A1 | 2/2012 | Fuhrman | |

FOREIGN PATENT DOCUMENTS

WO    2006091221 A2    8/2006

* cited by examiner

*Primary Examiner* — Abdullahi Nur
(74) *Attorney, Agent, or Firm* — Mark A. Logan; PatServe

(57) ABSTRACT

The present disclosure is directed to a method of particle size determination for particles suspended within a light-transmissive medium. The method includes directing a monochromatic light source into the medium and collecting from the medium a Raman-scattered light spectrum. The method includes analyzing the Raman spectrum to determine an amount of Tyndall scattering of the Raman spectrum caused by particles within the medium, and thus determine the size and the number of particles mediating the Tyndall scattering.

20 Claims, 8 Drawing Sheets

PARTICLE SIZE DETERMINATION USING RAMAN SPECTROSCOPY

CROSS-REFERENCE TO RELATED APPLICATION

The present application is related to and claims the priority benefit of U.S. Provisional Patent Application No. 62/408,108, filed on Oct. 14, 2016, the entire contents of which are incorporated herein by reference.

TECHNICAL FIELD

The present application relates generally to a method of particle size determination in a light-transmissive medium using a Raman spectroscopic apparatus.

BACKGROUND

Light scattered from a molecule may be elastically scattered or inelastically scattered. Most of the photons are elastically scattered and have the same frequency and wavelength as the incident light. This elastic scattering is Rayleigh scattering. A small fraction of the light, approximately 1 in 10,000,000 photons, is inelastically scattered at frequencies usually lower than the frequency of the incident light. The frequency of the inelastically scattered light is dependent upon the molecules doing the scattering. This inelastic scattering is Raman scattering.

Generally, Rayleigh scattering is mediated by particles far smaller than the wavelength of the light. The particle sizes are approximately less than 40 nanometers (nm). However, another type of elastic scattering, Tyndall scattering, is mediated by much larger particles, particles approximately in the range from 40 nm to 900 nm. In Tyndall scattering, as in Rayleigh scattering, the intensity of the scattered light is dependent upon the fourth power of the frequency of the incident light. Therefore, blue light is scattered more strongly than red light. Tyndall scattering may be mediated by particles in a light-transmissive colloid or fine suspension.

SUMMARY

The present disclosure is directed to a method of particle size determination for particles suspended within a light-transmissive medium. The method includes directing a monochromatic light source into the medium and collecting from the medium a Raman-scattered light spectrum. The method includes analyzing the Raman spectrum to determine an amount of Tyndall scattering of the Raman spectrum caused by particles within the medium, and thus determine the size and the number of particles mediating the Tyndall scattering.

BRIEF DESCRIPTION OF THE DRAWINGS

The present disclosure is explained in further detail below on the basis of the embodiments shown in the illustrations.

DETAILED DESCRIPTION

The methods and system disclosed in the present disclosure are directed to extracting particle size information of particles dispersed in a light-transmitting medium at the same time Raman spectra of the medium are acquired. In the disclosed methods, the Raman spectrum scattered by the medium—and not excitation (i.e., laser) light—is used as the light source to be scattered by the particles. Thus, the light transmitting medium will be the most useful source of light as in most cases it will generate the most intense Raman signal.

Key parameters associated with the measurement of particle size include the volume fraction of particles up to 1 micrometer (μm) in size, the intensity of the Raman bands generated by the medium and the particles, and the path length of the Raman collection.

The impact of particle scattering on the Raman spectra of the medium may be dependent on the path length of the laser light in the Raman probe. As such, immersion probes designed for longer working distances, for example, versions of Applicant's "Airhead" probe with a double bounce design, could be of benefit. For particles larger than 1 μm, probes with off-axis or dual collection capability may be employed, particularly where Mie scattering is the dominant effect.

The disclosed methods are performed using an apparatus including a monochromatic light source and a Raman probe including a spectrometer capable of capturing, storing to memory, and analyzing a Raman spectrum. The Raman probe may be an immersion type probe including a long path length for the monochromatic light to contact the medium. The Raman probe may be an immersion type probe having a multi-pass design wherein the monochromatic light source is directed through the medium multiple times by the use of reflective surfaces within the probe.

The medium containing the dispersed particles may be contained within a batch reactor into which one or more Raman probes is inserted. The medium may include a solute dissolved in a solvent, wherein under certain conditions the solute crystalizes through a nucleation process. The conditions for the nucleation process may include the temperature of the medium, the pressure within the batch reactor, or chemical additions to the medium. The particles dispersed in the medium may be the solute crystals resulting from the nucleation.

The monochromatic light source may be a laser with a wavelength from the ultra-violet region to the near infrared region. As non-limiting examples, wavelength values of the monochromatic light source may include 532 nm, 785 nm, and 933 nm.

Various embodiments of the disclosed methods will now be presented in conjunction with the figures which illustrate the embodiments.

Figure 1:
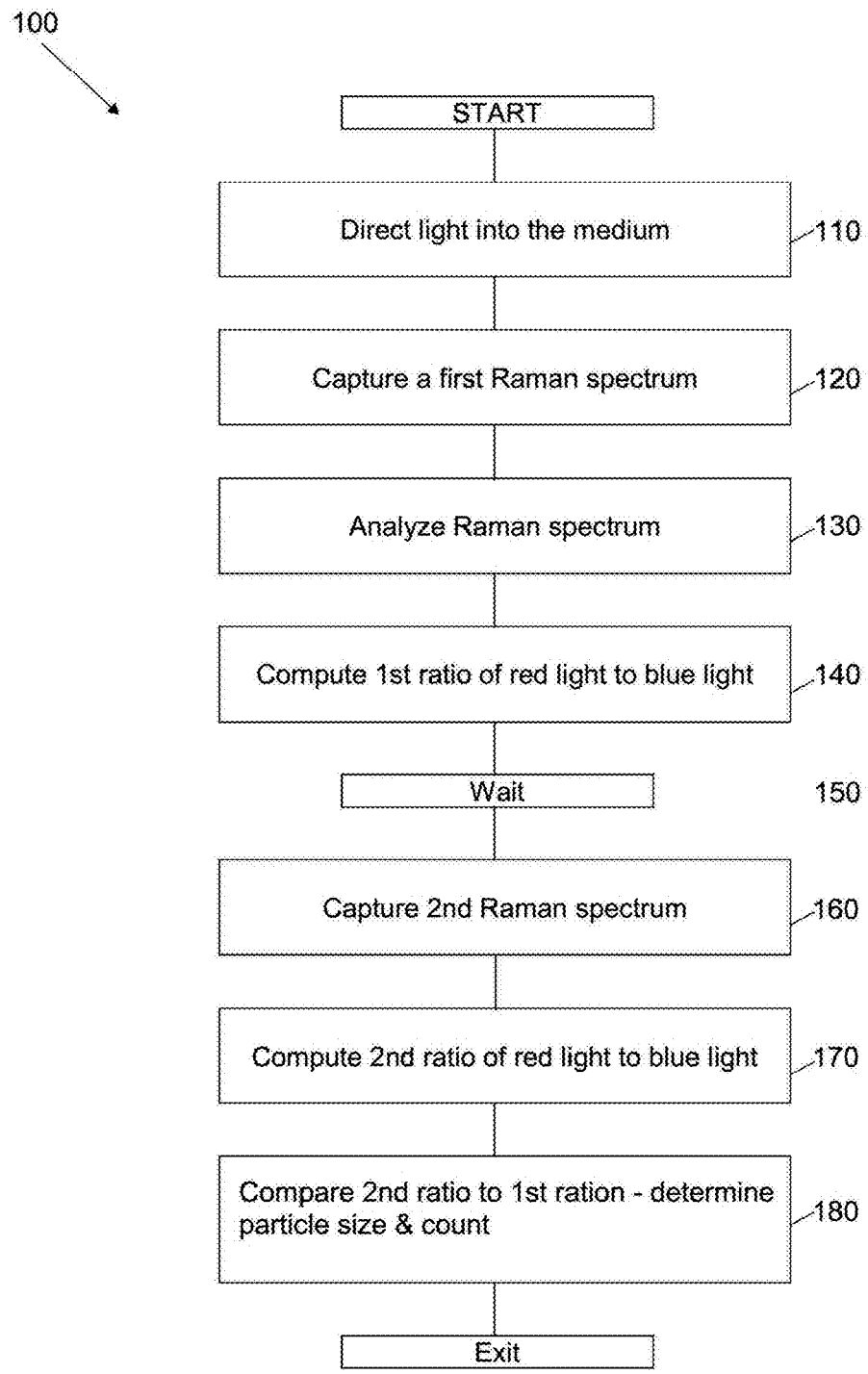
FIG. 1 shows a flow diagram of an embodiment of a disclosed method.

A method 100 according to at least one embodiment of the present disclosure is shown in FIG. 1. Method 100 is directed to determining particle size and particle count in a light-transmissive medium using at least two Raman spectra of the medium captured at different points in time.

The method 100 includes a step 110 of directing a monochromatic light source into the light-transmissive medium.

The medium and the particles dispersed within the medium may inelastically scatter the monochromatic light, and the method 100 includes a step 120 of collecting from the medium a first Raman spectrum using a Raman spectrometer.

The method 100 includes a step 130 of analyzing the first Raman spectrum to determine a relative composition of the matter in the medium having a Raman signature.

The method 100 includes a step 140 of calculating a first ratio of the red light in the first Raman spectrum to the blue light in the first Raman spectrum. Red light and blue light are not strictly defined regarding their wavenumbers or wavenumber ranges, but depend on the Raman spectrum obtained from the medium. Since the range of different solvents likely to be used in the medium will have Raman bands throughout the wavenumber range, a band of red light and a band of blue light may be selected based on the maximum difference in band position and on the intensity of each band.

Figure 3:
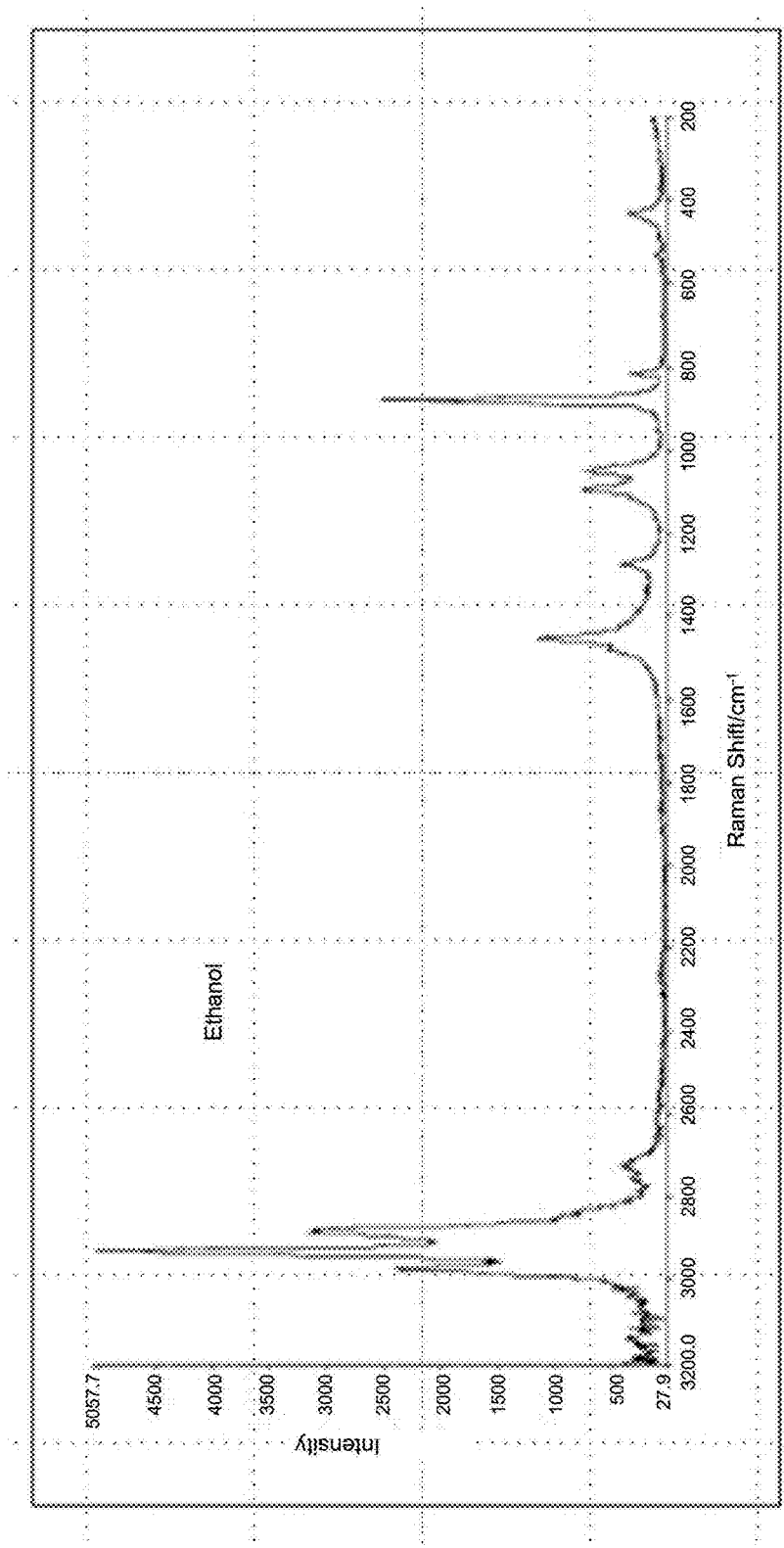
FIG. 3 shows a representative Raman spectrum of ethanol.

By way of example, FIG. 3 shows a Raman spectrum obtained from ethanol. In the Raman spectrum as shown in FIG. 3, the blue band used in the ratio calculation may be that part of the Raman spectrum around 900 wavenumbers. The red band used in the ratio calculation may be that part of the Raman spectrum around 2900 wavenumbers. These two bands would be the best combination to calculate the ratio of red light to blue light in the Raman spectrum and therefrom determine the Tyndall scattering within the medium. Therefore, the choice of the band of red light and the band of blue light used in the ratio calculation depends upon the Raman spectrum obtained from the medium, and this choice may vary in each application of the disclosed method.

The method 100 may include a step 150 of waiting a pre-determined period of time, during which particles may form within the medium.

The method 100 may include a step 160 of directing the monochromatic light into the medium after the pre-determined period and obtaining from the medium a second Raman spectrum using the Raman spectrometer.

The method 100 may include a step 170 of calculating a second ratio of the red light in the second Raman spectrum to the blue light in the second Raman spectrum. The band of red light and the band of blue light used in the calculation of the second ratio are the same as the band of red light and the band of blue light used in the calculation of the first ratio. That is, the wavenumber range of the red band is the same in each calculation, and the wavenumber range of the blue band is the same in each calculation, though the intensity data for each band come from each respective Raman spectrum.

The method 100 may include a step 180 of comparing the second ratio to the first ratio and of determining particle size information from the comparison of the ratios. Particle size information is obtained from an analysis of the Tyndall scattering of the Raman spectrum as shown in the comparison of the two ratios.

Tyndall scattering is stronger for blue light than for red. That is, more blue light than red light will be scattered away from the spectrometer. Therefore, if the ratio of red light to blue light in the second Raman spectrum is greater than the ratio of red light to blue light in the first Raman spectrum, then there are more particles sized approximately from 40 nm to 900 nm in the medium when the second Raman spectrum was captured than when the first Raman spectrum was captured. This ratio change could indicate, for example, that a nucleation of crystals had taking place in the medium during the pre-determined period of step 150.

Conversely, if the ratio of red light to blue light in the second Raman spectrum is less than the ratio of red light to blue light in the first Raman spectrum, then there are fewer particles sized approximately from 40 nm to 900 nm in the medium when the second Raman spectrum was captured than when the first Raman spectrum was captured. This ratio change could indicate, for example, that the particles within the medium have grown greater than 1 μm in size and are no longer mediating Tyndall scattering of the Raman spectrum.

Figure 4:
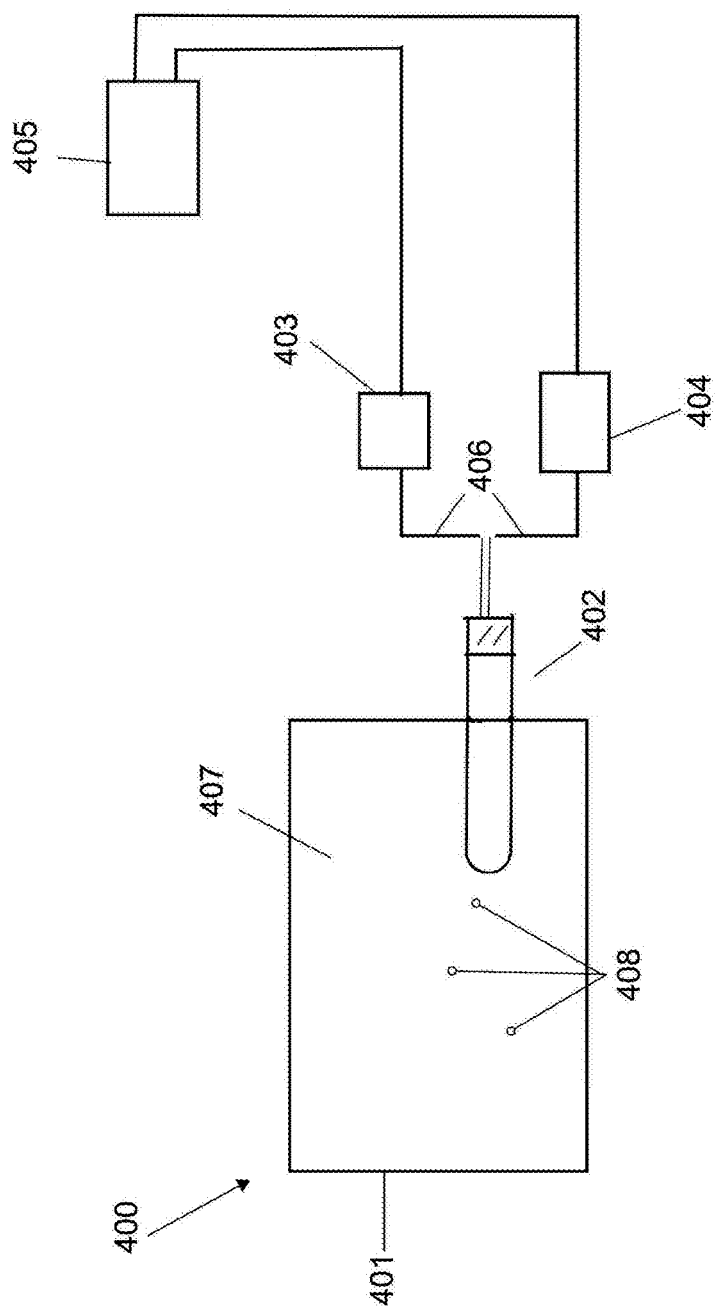
FIG. 4 shows a system for determining particle size according to the present disclosure.

In another embodiment of the present disclosure, a method 200 of controlling a crystallization process within a light-transmissive medium is disclosed. In such an embodiment, the medium may be contained within a batch reactor. A batch reactor 400 is shown in FIG. 4. Any of the flanged openings 401 on the batch reactor 400 may serve as a connection point for a Raman probe used in the present method.

Figure 2:
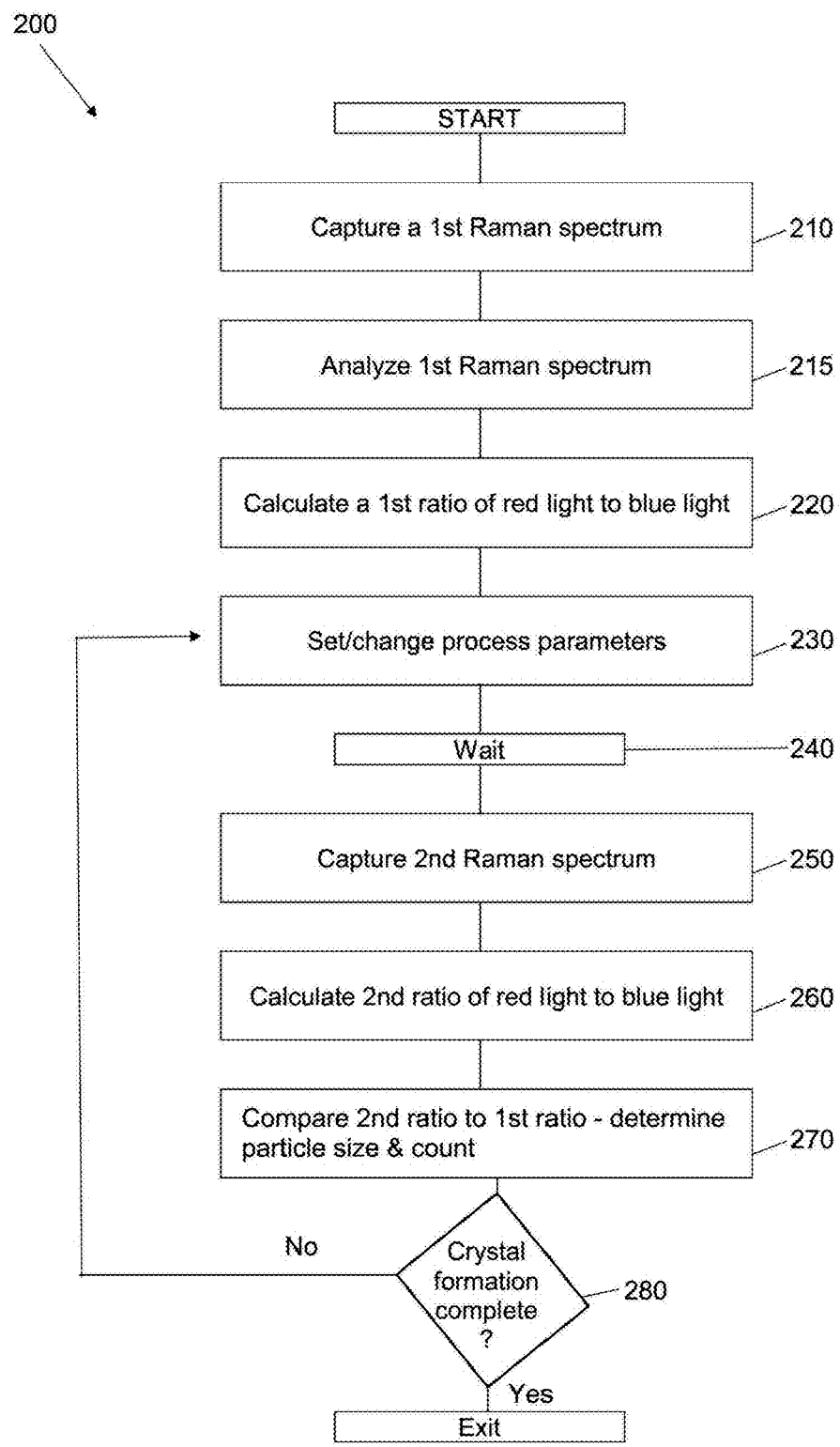
FIG. 2 shows a flow diagram of a second embodiment of a disclosed method.

The method 200 according to at least one embodiment of the present disclosure is shown in FIG. 2. The method 200 may be used in a process control loop to monitor a crystallization process by periodically capturing Raman spectra, calculating from the Raman spectra a ratio of the red light to the blue light, and providing particle size information to the control loop.

The method 200 includes a step 210 of directing a monochromatic light source into the light-transmissive medium and collecting from the medium a first Raman spectrum using a Raman spectrometer.

The method 200 includes a step 215 of analyzing the first Raman spectrum to determine a relative composition of the matter in the medium having a Raman signature.

The method 200 includes a step 220 of calculating a first ratio of the red light in the first Raman spectrum to the blue light in the first Raman spectrum. The band of red light and the band of blue light used in the first ratio calculation will be selected based on the maximum difference in band position and on the intensity of each band.

The method 200 includes a step 230 of optionally setting or changing any process parameters of the crystallization process. The process parameters may include the temperature of the medium, the pressure within the batch reactor, or a chemical addition to the medium, among others. The process parameter change may be used to increase or decrease crystal nucleation within the medium as desired.

The method 200 includes a step 240 of waiting a pre-determined period of time, during which crystal nucleation may occur within the medium.

The method 200 includes a step 250 of directing a monochromatic light source into the light-transmissive medium and collecting from the medium a second Raman spectrum using the Raman spectrometer.

The method 200 includes a step 260 of calculating a second ratio of the red light in the second Raman spectrum to the blue light in the second Raman spectrum. The band of red light and the band of blue light used in the calculation of the second ratio are the same as the band of red light and the band of blue light used in the calculation of the first ratio. That is, the wavenumber range of the red band is the same in each calculation, and the wavenumber range of the blue band is the same in each calculation, though the intensity data for each band come from the respective Raman spectrum.

The method 200 includes a step 270 of comparing the second ratio to the first ratio and of determining crystal nucleation information from the comparison of the ratios. The crystal nucleation information is obtained from an analysis of the Tyndall scattering of the Raman spectrum as shown in the comparison of the two ratios.

The method 200 includes a step 280 of determining from the crystal nucleation information determined in the step 270 whether the process should continue or whether the process has reached a point of completion. This determination is specific to the process which method 200 is monitoring. If the process should continue, the steps of the method 200 are repeated beginning from the step 230.

In an embodiment of the disclosed method, the analysis of the Tyndall scattering method may be used in conjunction with a Raman analysis to identify specific nucleation occurring within the process. For example, a crystallization of a particular molecule make take one of several forms, each form having a unique Raman signature. The Raman analysis can be used to identify the particular crystals forming in the medium, and the Tyndall analysis can be used to identify the size and amount of the crystals forming. In such an embodiment, the method may include using two separate apparatuses, wherein one apparatus provides particle size information and the second apparatus provides polymorph identification at the same time.

In another embodiment, the disclosed methods may be used to monitor a process in which nucleation is not desired. In such an embodiment of the method, it is expected the ratio of red light in a captured Raman spectrum to blue light in a captured Raman spectrum stays nearly constant as a function of time. However, changes in the ratio of red light to blue light between the first captured Raman spectrum and the second captured Raman spectrum may indicate an undesired crystal nucleation is occurring within the medium.

FIG. 4 shows an embodiment of a system 400 for determining particle size of particles in a light-transmissive medium according to the present disclosure. The system 400 may include a Raman probe 402 embodied to fit into a batch reactor 401. The system 400 may include a monochromatic light source 403 coupled to the Raman probe 402 via a fiber optic connection 406. The system 400 may include a Raman spectrum detector 404 connected to the Raman probe via a fiber optic connection 406. The system 400 may include a controller 405 configured to analyze the Raman spectra received by the Raman spectrum detector 404 to determine the content of the medium 407 and the size and amount of the particles 408 dispersed in the medium according to methods disclosed in the present disclosure. The controller 405 may also be configured to control the monochromatic light source 403 and the Raman spectrum detector 404 for the acquisition of Raman spectra.

Batch reactor 401 may include other connections (not shown in FIG. 4) for pressure sensors and temperature sensors, for example. Batch reactor 401 may also include process connections for the inflow and outflow of various solvents, reagents, etc.

In certain embodiments, the system 400 may include more than one Raman probe and connections from the monochromatic light source and the Raman spectrum detector to the additional Raman probes. In one such embodiment, one Raman probe may be used for particle size determination and a second Raman probe may be used for Raman content analysis of the medium. These separate probes may provide particle size determination and polymorph identification of crystals at the same time, for example.

Figure 5:
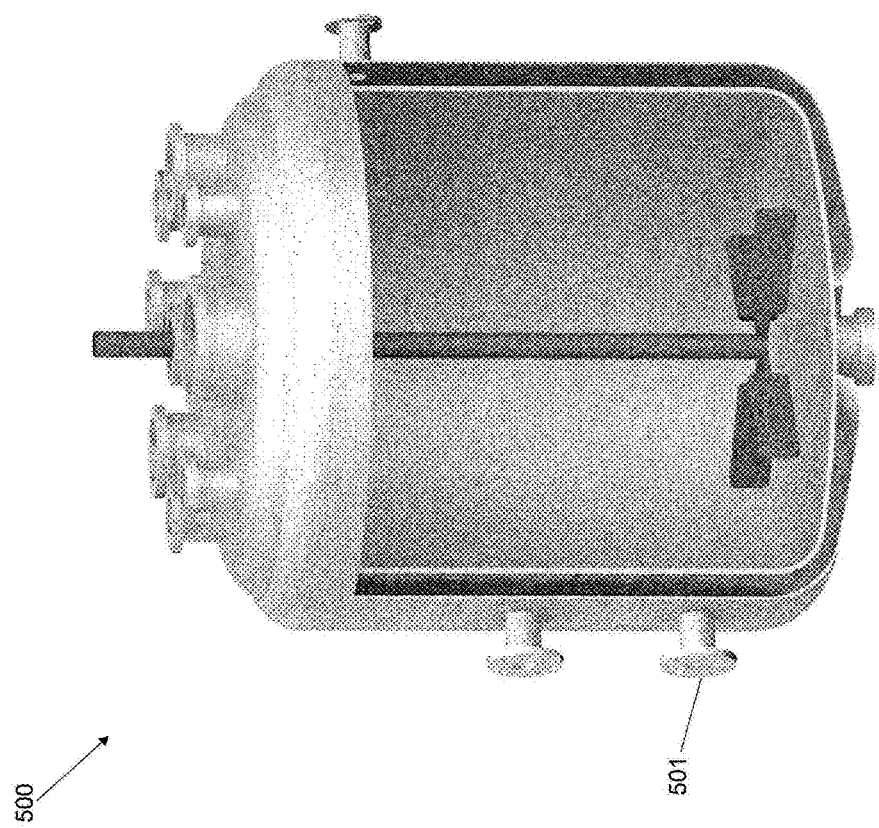
FIG. 5 shows a batch reactor.

FIG. 5 shows an embodiment of a batch reactor 500 according to the present disclosure. The batch reactor may include one or more connections points 501 for the connection of Raman probes, temperature sensors, liquid lines, etc.

Figure 6:
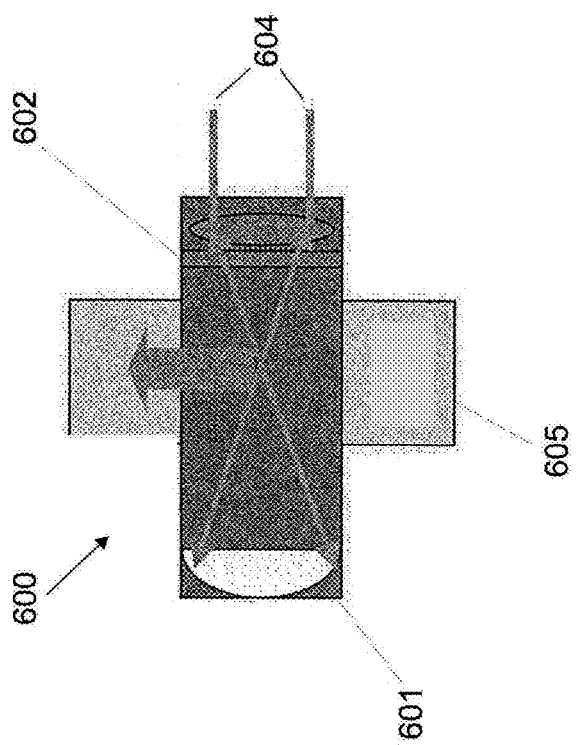
FIG. 6 shows a Raman probe embodied as an extended path reflection probe.

FIG. 6. shows an embodiment of an extended-path reflection Raman probe 600 according to the present disclosure. The probe 600 monochromatic light enters the probe 600 via fiber optic connections 604 and passes through focusing optics 603 and sapphire window 602. The monochromatic light crosses through sample flow 605 to the interior reflector 601. The reflector 601 reflects the monochromatic light back through the sample flow 605 to the sapphire window 602 and the focusing optics 604. Thus the monochromatic light makes multiple passes through the sample flow. The Raman spectra are collected from the sample flow via the sapphire window 602 and the focusing optics 603 and are sent via fiber optic connection 405 to the collector (not shown) for further processing.

Figure 7:
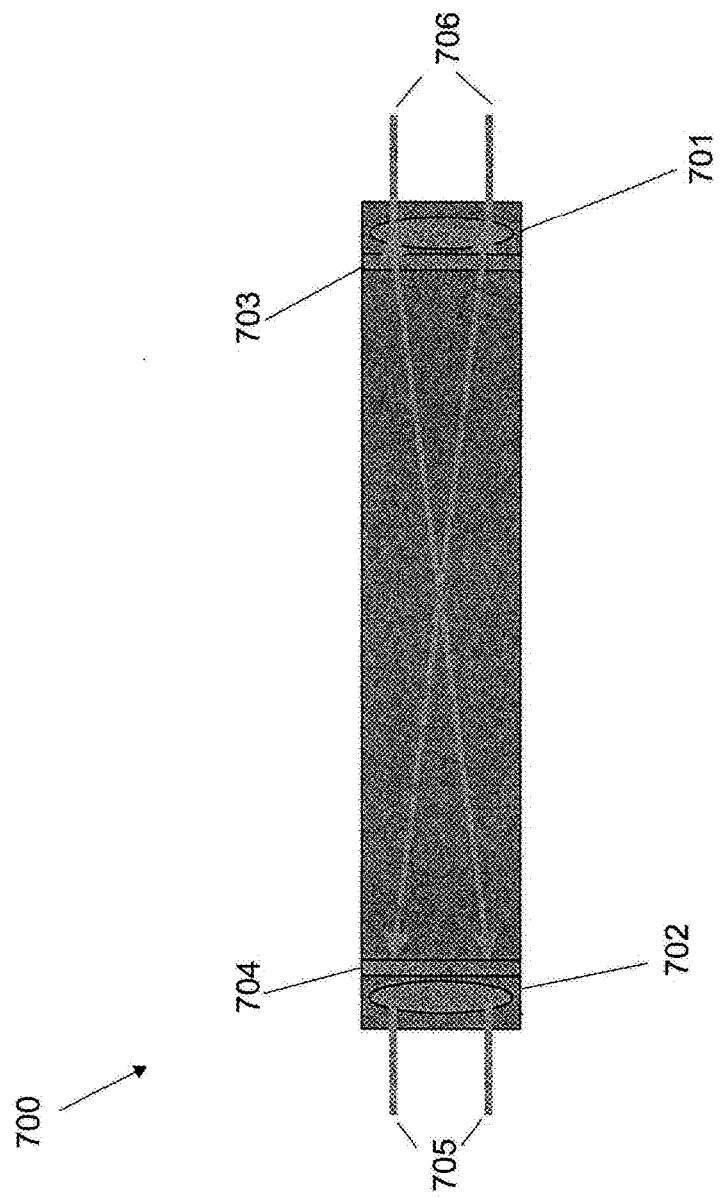
FIG. 7 shows a Raman probe embodied as an extended path probe.

FIG. 7 shows an embodiment of an extended path Raman probe 700 according to the present disclosure. Probe 700 includes focusing optics 701, 702, sapphire windows 703, 704, and fiber options connections 705, 706 at both ends of the probe. The elongated probe body and the double paths for the monochromatic laser provide a longer path for exposure of the medium to the monochromatic light.

Figure 8:
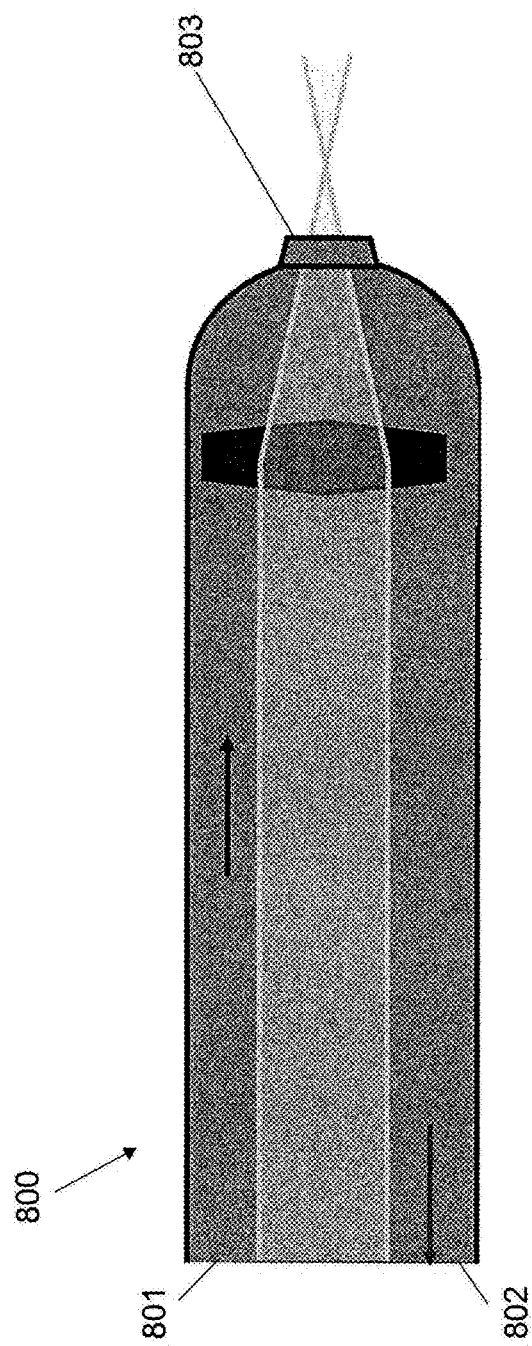
FIG. 8 shows a Raman embodied as a reflection probe.

FIG. 8 shows an embodiment of a reflection Raman probe according to the present disclosure. Probe 800 includes a path 801 for the monochromatic light. The monochromatic light is transmitted into the medium via the focusing optics 803. The Raman spectrum is collected from the medium through the focusing optics 803 and it sent back to the collection apparatus via return path 802.

The invention claimed is:

1. A method for determining the size of particles dispersed in a light-transmissive medium, comprising:
   directing an excitation light into the medium, wherein the excitation light is monochromatic;
   collecting from the medium a first Raman spectrum using a Raman spectrometer;
   analyzing the first Raman spectrum to determine a composition of the medium;
   computing a first ratio of red light in the first Raman spectrum to blue light in the first Raman spectrum;
   waiting a pre-determined period of time;
   after the pre-determined period, directing the excitation light into the medium and collecting from the medium a second Raman spectrum using the Raman spectrometer;
   computing a second ratio of red light in the second Raman spectrum to blue light in the second Raman spectrum;
   comparing the second ratio to the first ratio; and
   determining the size and a count of particles dispersed in the medium based on the comparison of the second ratio to the first ratio.

2. The method of claim 1, wherein the excitation light is a laser operating at 532 nanometers (nm), 785 nm, or 933 nm.

3. The method of claim 1, wherein the red light in the first Raman spectrum and the red light in the second Raman spectrum have a first wavenumber range, and wherein the blue light in the first Raman spectrum and the blue light in the second Raman spectrum have a second wavenumber range,
   wherein the first wavelength range has greater wavenumbers than the second wavenumber range,
   wherein the first wavenumber range and the second wavenumber range are selected based on an intensity of light within each respective wavenumber range in the first Raman spectrum and on the distance of the first wavenumber range from the second wavenumber range in the first Raman spectrum.

4. The method of claim 1, wherein the second ratio being greater than the first ratio indicates more particles sized approximately from 40 nm to 900 nm were dispersed in the medium when the second Raman spectrum was collected.

5. The method of claim 1, wherein the second ratio being less than the first ratio indicates fewer particles sized approximately from 40 nm to 900 nm were dispersed in the medium when the second Raman spectrum was collected.

6. A method for controlling a crystal nucleation process within a light-transmissive medium, comprising:
    directing an excitation light into the medium, wherein the excitation light is monochromatic;
    collecting from the medium a first Raman spectrum using a Raman spectrometer;
    analyzing the first Raman spectrum to determine a composition of the medium;
    computing a first ratio of red light in the first Raman spectrum to blue light in the first Raman spectrum;
    waiting a pre-determined period of time;
    after the pre-determined period, directing the excitation light into the medium;
    collecting from the medium a second Raman spectrum using the Raman spectrometer;
    computing a second ratio of red light in the second Raman spectrum to blue light in the second Raman spectrum;
    comparing the second ratio to the first ratio;
    determining the size and a count of particles dispersed in the medium based on the comparison of the second ratio to the first ratio; and
    repeating the waiting, the directing, the collecting, the computing, the comparing, and the determination of particle size and count until a pre-determined crystal nucleation state is reached.

7. The method of claim 6, wherein the excitation light is a laser operating at 532 nm, 785 nm, or 933 nm.

8. The method of claim 6, wherein the red light in the first Raman spectrum and the red light in the second Raman spectrum have a first wavenumber range, and wherein the blue light in the first Raman spectrum and the blue light in the second Raman spectrum have a second wavenumber range,
    wherein the first wavelength range has greater wavenumbers than the second wavenumber range,
    wherein the first wavenumber range and the second wavenumber range are selected based on an intensity of light within each respective wavenumber range in the first Raman spectrum and on the distance of the first wavenumber range from the second wavenumber range in the first Raman spectrum.

9. The method of claim 6, wherein the second ratio being greater than the first ratio indicates more particles sized approximately from 40 nm to 900 nm were dispersed in the medium when the second Raman spectrum was collected.

10. The method of claim 6, wherein the second ratio being less than the first ratio indicates fewer particles sized approximately from 40 nm to 900 nm were dispersed in the medium when the second Raman spectrum was collected.

11. The method of claim 6, further comprising analyzing the second Raman spectrum to determine crystal polymorph species dispersed in the medium.

12. The method of claim 6, further comprising:
    after the computing of the first ratio, changing a parameter of the nucleation process.

13. A system for determining particle size in a light-transmissive medium, comprising:
    at least one probe embodied to direct laser light into a sample including particles dispersed in a light-transmissive medium and to collect Raman emission spectra from the sample, wherein the Raman emission spectra illuminate the dispersed particles;
    a detector configured to receive the collected Raman emission spectra from the sample; and
    a processor configured to analyze the collected Raman emission spectra to determine the size of particles resulting from the illumination of the particles by the Raman emission spectra,
    wherein the processor is further configured to determine particle size by:
        analyzing the first Raman spectrum to determine a composition of the medium;
        computing a first ratio of red light in the first Raman spectrum to blue light in the first Raman spectrum;
        computing a second ratio of red light in the second Raman spectrum to blue light in the second Raman spectrum;
        comparing the second ratio to the first ratio; and
        determining the size and a count of particles dispersed in the medium based on the comparison of the second ratio to the first ratio.

14. The system of claim 13, wherein the determination of particle size is based on Tyndall scattering.

15. The system of claim 13, wherein the determination of particle size is indicative of nucleation.

16. The system of claim 13, wherein the probe includes an extended path length to enhance sensitivity.

17. The system of claim 13, wherein the processor is configured to control the probe and the detector.

18. The system of claim 13, wherein the processor is configured to control a nucleation process by:
    analyzing the first Raman spectrum to determine a composition of the medium;
    computing a first ratio of red light in the first Raman spectrum to blue light in the first Raman spectrum;
    computing a second ratio of red light in the second Raman spectrum to blue light in the second Raman spectrum;
    comparing the second ratio to the first ratio;
    determining the size and a count of particles dispersed in the medium based on the comparison of the second ratio to the first ratio; and
    repeating the computing a second ratio, the comparing, and the determining until a predetermined crystal nucleation state is reached.

19. The system of claim 13, further comprising a vessel embodied to hold the light-transmissive medium, wherein the vessel is configured with at least one process connection to enable a connection of the at least one probe.

20. The system of claim 13, further comprising a second probe embodied to direct laser light into the sample and to collect a second Raman emission spectrum from the sample, wherein the second Raman emission spectrum illuminates the dispersed particles, wherein the at least one probe is used to determine particle size, and wherein the second probe is used to identify crystal polymorph species dispersed in the medium.

* * * * *